United States Patent
Thevelein et al.

(10) Patent No.: US 10,612,049 B2
(45) Date of Patent: Apr. 7, 2020

(54) CAUSATIVE GENES CONFERRING ACETIC ACID TOLERANCE IN YEAST

(71) Applicants: VIB vzw, Ghent (BE); Katholieke Universiteit Leuven, K.U. Leuven R & D, Leuven (BE)

(72) Inventors: Johan Thevelein, Blanden (BE); Jean-Paul Meijnen, Rhenen (NL); Maria Remedios Foulquié Moreno, Brussels (BE)

(73) Assignees: VIB vzw, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 29 days.

(21) Appl. No.: 15/527,736

(22) PCT Filed: Nov. 24, 2015

(86) PCT No.: PCT/EP2015/077541
§ 371 (c)(1),
(2) Date: May 18, 2017

(87) PCT Pub. No.: WO2016/083397
PCT Pub. Date: Jun. 2, 2016

(65) Prior Publication Data
US 2017/0356013 A1    Dec. 14, 2017

(30) Foreign Application Priority Data
Nov. 24, 2014 (EP) .................................. 14194443

(51) Int. Cl.
| | | |
|---|---|---|
| C12P 7/06 | (2006.01) |
| C12N 9/08 | (2006.01) |
| C12N 1/19 | (2006.01) |
| C07K 14/395 | (2006.01) |
| C12P 7/10 | (2006.01) |
| C12N 1/18 | (2006.01) |
| C12N 15/81 | (2006.01) |

(52) U.S. Cl.
CPC .............. *C12P 7/10* (2013.01); *C07K 14/395* (2013.01); *C12N 1/18* (2013.01); *C12N 9/0065* (2013.01); *C12N 15/81* (2013.01); *C12Y 111/01015* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2015/0218592 A1    8/2015 Kondo et al.

OTHER PUBLICATIONS

Uniprot, Accession No. W0TAU1, 2014, www.uniprot.org.*
Portuguese Yeast Culture Collection, Deposit No. PYCC 4542, 1989, pycc.bio-aware.com.*
Meijnen et al., Polygenic analysis and targeted improvement of the complex trait of high acetic acid tolerance in the yeast *Saccharomyces cerevisiae*, Biotechnol. Biofules, 2016, 9:5.*
GenBank, Accession No. AY558298, 2007, www.ncbi.nlm.gov.*
GenBank, Accession No. AY557820, 2007, www.ncbi.nlm.gov.*
GenBank, Accession No. Z72805.1, 1997, www.ncbi.nlm.gov.*
Brat et al., Functional Expression of a Bacterial Xylose Isomerase in *Saccharomyces cerevisiae*, Appl. Environ. Microbiol., 2009, 75, 2304-11.*
Xinqing Zhao et al., Advances in functional genomics studies underlying acetic acid tolerance of *Saccharomyces cerevisiae*, Chinese J. Biotechnol., vol. 30, No. 3, Mar. 2014, pp. 368-380, ISSN: 1000-3061, Database Medline [Online] US National Library of Medicine, Database accession No. NLM25007573, XP002754426.*
Giannattasio S et al: "Acid stress adaptation protects *Saccharomyces cerevisiae* from acetic acid-induced programmed cell death", Gene, Elsevier, Amsterdam, NL, vol. 354, Jul. 18, 2005 (Jul. 18, 2005), pp. 93-98, XP025394404, ISSN: 0378-1119.
Database UniProt [Online] Jul. 9, 2014 (Jul. 9, 2014), "SubName: Full=Dot5p (ECO:0000313|EMBL:EWG90543.1);", retrieved from EBI accession No. UNIPROT:A0A024XNC0 Database accession No. A0A024XNC0.
Written Opinion for PCT/EP2015/077541, dated Jan. 2015.
Abbott, D.A. et al. (2007). Generic and specific transcriptional responses to different weak organic acids in anaerobic chemostat cultures of *Saccharomyces cerevisiae*. Fems Yeast Research 7, 819-833.
Almeida, J.R.M. et al. (2007). Increased tolerance and conversion of inhibitors in lignocellulosic hydrolysates by *Saccharomyces cerevisiae*. Journal of Chemical Technology and Biotechnology 82, 340-349.
Baudin, A., Ozier-Kalogeropoulos, O., Denouel, A., Lacroute, F. & Cullin, C. (1993). A simple and efficient method for direct gene deletion in *Saccharomyces cerevisiae*. Nucleic Acids Res 21, 3329-3330.
Bellissimi, E., van Dijken, J.P., Pronk, J.T. & van Maris, A.J.A. (2009). Effects of acetic acid on the kinetics of xylose fermentation by an engineered, xylose-isomerase-based *Saccharomyces cerevisiae* strain. Fems Yeast Research 9, 358-364.
Casey, E., Sedlak, M., Ho, N.W. & Mosier, N.S. (2010). Effect of acetic acid and pH on the cofermentation of glucose and xylose to ethanol by a genetically engineered strain of *Saccharomyces cerevisiae*. Fems Yeast Research 10, 385-393.
Claesen, J., Clement, L., Shkedy, Z., Foulquie-Moreno, M.R. & Burzykowski, T. (2013). Simultaneous mapping of multiple gene Loci with pooled segregants. PLoS One 8, e55133.
Deutschbauer, A.M. & Davis, R.W. (2005). Quantitative trait loci mapped to single-nucleotide resolution in yeast. Nat Genet 37, 1333-1340.
Duitama, J. et al. (2012). Fosmid-based whole genome haplotyping of a HapMap trio child: evaluation of Single Individual Haplotyping techniques. Nucleic Acids Res 40, 2041-53.

(Continued)

*Primary Examiner* — Robert B Mondesi
*Assistant Examiner* — Todd M Epstein
(74) *Attorney, Agent, or Firm* — NLO; Catherine Shulz; Tamara Stegmann

(57) ABSTRACT

The present invention relates to genes conferring acetic acid tolerance in yeast. More specifically, the invention relates to the use of DOT5, preferably in combination with CUP2 and/or HAA1 to obtain acid tolerance in yeast. Even more preferably, the invention relates to specific alleles of said genes, and to yeast strains comprising said specific alleles.

7 Claims, 7 Drawing Sheets

Specification includes a Sequence Listing.

(56) References Cited

OTHER PUBLICATIONS

Ehrenreich, I.M. et al. (2010). Dissection of genetically complex traits with extremely large pools of yeast segregants. Nature 464, 1039-1042.

Fernandes, A.R., Mira, N.P., Vargas, R.C., Canelhas, I. & Sa-Correia, I. (2005). *Saccharomyces cerevisiae* adaptation to weak acids involves the transcription factor Haa1p and Haa1p-regulated genes. Biochem Biophys Res Commun 337, 95-103.

Flint, J. & Mott, R. (2001). Finding the molecular basis of quantitative traits: successes and pitfalls. Nat Rev Genet 2, 437-445.

Gietz, R.D., Schiestl, R.H., Willems, A.R. & Woods, R.A. (1995). Studies on the transformation of intact yeast cells by the LiAc/SS-DNA/PEG procedure. Yeast 11, 355-360.

Glazier, A.M., Nadeau, J.H. & Aitman, T.J. (2002). Finding genes that underlie complex traits. Science 298, 2345-2349.

Hasunuma, T. et al. (2011). Metabolic pathway engineering based on metabolomics confers acetic and formic acid tolerance to a recombinant xylose-fermenting strain of *Saccharomyces cerevisiae*. Microb Cell Fact 10, 2.

Hoffman, C.S. & Winston, F. (1987). A ten-minute DNA preparation from yeast efficiently releases autonomous plasmids for transformation of *Escherichia coli*. Gene 57, 267-272.

Huang, H. et al. (2011). Identification of crucial yeast inhibitors in bio-ethanol and improvement of fermentation at high pH and high total solids. Bioresour Technol 102, 7486-7493.

Hubmann, G. et al. (2013). Quantitative trait analysis of yeast biodiversity yields novel gene tools for metabolic engineering. Metab Eng 17, 68-81.

Huxley, C., Green, E.D. & Dunham, I. (1990). Rapid assessment of *S. cerevisiae* mating type by PCR. Trends Genet 6, 236.

Johnston, J.R. (1994). Molecular Genetics of Yeast: A Practical Approach, (Oxford University Press Inc., New York.

Koppram, R., Albers, E. & Olsson, L. (2012). Evolutionary engineering strategies to enhance tolerance of xylose utilizing recombinant yeast to inhibitors derived from spruce biomass. Biotechnol Biofuels 5, 32.

Li, B.Z. & Yuan, Y.J. (2010). Transcriptome shifts in response to furfural and acetic acid in *Saccharomyces cerevisiae*. Appl Microbiol Biotechnol 86, 1915-1924.

Lumtong, S., Sumpradit, T., Kitpreechavanich, V., Tuntirungkij, M., Seki, T. and Yoshida, T. (2000). Effect of Acetic acid on growth and ethanol fermentation of xylose fermenting yeasts and *Saccharomyces cerevisiae*.Kastaert J. (Nat. Sci) 34, 64-73.

Matsushika, A. & Sawayama, S. (2012). Characterization of a Recombinant Flocculent *Saccharomyces cerevisiae* Strain That Co-Ferments Glucose and Xylose: II. Influence of pH and Acetic Acid on Ethanol Production. Appl Biochem Biotechnol.

Mira, N.P., Palma, M., Guerreiro, J.F. & Sa-Correia, I. (2010a). Genome-wide identification of *Saccharomyces cerevisiae* genes required for tolerance to acetic acid. Microb Cell Fact 9, 79-91.

Mira, N.P., Becker, J.D. & Sa-Correia, I. (2010b). Genomic expression program involving the Haa1p-regulon in *Saccharomyces cerevisiae* response to acetic acid. OMICS 14, 587-601.

Narendranath, N.V., Thomas, K.C. & Ingledew, W.M. (2001). Effects of acetic acid and lactic acid on the growth of *Saccharomyces cerevisiae* in a minimal medium. J Ind Microbiol Biotechnol 26, 171-177.

Olsson, L. and Hahn-Hägerdal, B. (1993). Fermentative performance of bacteria and yeast in lignocellulose hydrolysates. Process Biochem. 28, 249-257.

Parts, L. et al. (2011). Revealing the genetic structure of a trait by sequencing a population under selection. Genome Res.

Sherman, F. & Hicks, J. (1991). Micromanipulation and dissection of asci. Methods Enzymol 194, 21-37.

Steinmetz, L.M. et al. (2002). Dissecting the architecture of a quantitative trait locus in yeast. Nature 416, 326-330.

Swinnen, S. et al. (2012). Identification of novel causative genes determining the complex trait of high ethanol tolerance in yeast using pooled-segregant whole-genome sequence analysis. Genome Res 22, 975-984.

Taherzade, M.J., Niklasson, C. & Lidén, G. (1997). Acetic acid—friend of foe in anaerobic batch conversion of glucose to ethanol by *Saccharomyces cerevisiae*. Chemical Engineering Science 52, 2653-2659.

Tanaka, K., Ishii, Y., Ogawa, J. and Shima, J. (2012). Enhancement of acetic acid tolerance in *Saccharomyces cerevisiae* by overexpression of the HAA1 gene, encoding a transcription factor. Appl. Environ. Microbiol. 78, 8161-8163.

Wach, A. (1996). PCR-synthesis of marker cassettes with long flanking homology regions for gene disruptions in *S. cerevisiae*. Yeast 12, 259-265.

Wright, J. et al. (2011). Batch and continuous culture-based selection strategies for acetic acid tolerance in xylose-fermenting *Saccharomyces cerevisiae*. Fems Yeast Research.

Zhang, J.G. et al. (2011). Improvement of acetic acid tolerance and fermentation performance of *Saccharomyces cerevisiae* by disruption of the FPS1 aquaglyceroporin gene. Biotechnol Lett 33, 277-284.

\* cited by examiner

A

B

A

SEQUENCE LISTING

```
<160> NUMBER OF SEQ ID NOS: 10

<210> SEQ ID NO 1
<211> LENGTH: 648
<212> TYPE: DNA
<213> ORGANISM: Saccharomyces cerevisiae

<400> SEQUENCE: 1
atgggtgaag cactacgtag atcaaccagg attgcaacat ccaaaagaat gttggaagag      60
gaagagtcca aactggcccc tatttcgaca ccggaagtgc ctaagaaaaa aatcaagaca     120
```

```
ggtcctaaac ataacgctaa acaagcagta gttaaagagg caaataggtc atctgatgtt      180
aacgaattag agataggcga tcctattcct gatttgagtc ttttaaatga agataatgac      240
tctatctcct tgaagaaaat caccgaaaat aacagagttg tggtgttttt tgtgtatccc      300
agggcaagca cgcctggttg tactagacag gcctgtggat ttcgtgacaa ttaccaggaa      360
ctcaagaaat atgctgctgt ctttggactg agtgcagatt ctgtgacatc ccagaaaaag      420
tttcagagta acaaaatttt gccatatcat ttactaagcg attcaaagag agagtttatt      480
gggttgctag gagctaaaaa aacgccactt tctggttcta ttagatcgca tttcattttt      540
gttgatggga agttaaaatt caaaagagtt aagatatcac cagaagttag tgtaaatgac      600
gccaaaaagg aggttttaga agtcgctgaa aagtttaaag aagaatga                  648
```

<210> SEQ ID NO 2
<211> LENGTH: 215
<212> TYPE: PRT
<213> ORGANISM: Saccharomyces cerevisiae

<400> SEQUENCE: 2

Met Gly Glu Ala Leu Arg Arg Ser Thr Arg Ile Ala Thr Ser Lys Arg
1               5                   10                  15

Met Leu Glu Glu Glu Ser Lys Leu Ala Pro Ile Ser Thr Pro Glu
            20                  25                  30

Val Pro Lys Lys Lys Ile Lys Thr Gly Pro Lys His Asn Ala Lys Gln
        35                  40                  45

Ala Val Val Lys Glu Ala Asn Arg Ser Ser Asp Val Asn Glu Leu Glu
    50                  55                  60

Ile Gly Asp Pro Ile Pro Asp Leu Ser Leu Leu Asn Glu Asp Asn Asp
65                  70                  75                  80

Ser Ile Ser Leu Lys Lys Ile Thr Glu Asn Asn Arg Val Val Val Phe
                85                  90                  95

Phe Val Tyr Pro Arg Ala Ser Thr Pro Gly Cys Thr Arg Gln Ala Cys
            100                 105                 110

Gly Phe Arg Asp Asn Tyr Gln Glu Leu Lys Lys Tyr Ala Ala Val Phe
        115                 120                 125

Gly Leu Ser Ala Asp Ser Val Thr Ser Gln Lys Lys Phe Gln Ser Lys
    130                 135                 140

Gln Asn Leu Pro Tyr His Leu Leu Ser Asp Ser Lys Arg Glu Phe Ile
145                 150                 155                 160

Gly Leu Leu Gly Ala Lys Lys Thr Pro Leu Ser Gly Ser Ile Arg Ser
                165                 170                 175

His Phe Ile Phe Val Asp Gly Lys Leu Lys Phe Lys Arg Val Lys Ile
            180                 185                 190

Ser Pro Glu Val Ser Val Asn Asp Ala Lys Lys Glu Val Leu Glu Val
        195                 200                 205

Ala Glu Lys Phe Lys Glu Glu
    210                 215

<210> SEQ ID NO 3
<211> LENGTH: 678
<212> TYPE: DNA
<213> ORGANISM: Saccharomyces cerevisiae

<400> SEQUENCE: 3

```
atggtcgtaa ttaacggggt caaatatgcc tgtgaaacgt gtatcagggg tcacagggcg      60
gcgcagtgta ctcacactga tggtccgcta cagatgatca gacgcaaggg aagaccatcg     120
```

```
accacatgtg gccattgtaa agagctgaga agaaccaaga acttcaaccc atccggtggg        180
tgcatgtgtg cctctgcacg acggccagct gttggcagcg aggaagatga aacacgatgt        240
cgttgtgatg agggtgaacc ttgtaaatgt cataccaaga ggaaaagcag ccggaaatca        300
aagggagggt catgccacag aagggcaaat gatgaagcag cgcatgtcaa tggtctcggt        360
attgcagatc tggacgttct tttgggccta aatggtcgct cgtcggatgt agacatgaca        420
accacattgc cgagtttgaa gccacctctg caaaacggag aaattaaggc cgacagcatt        480
gacaatcttg atttggcttc cctcgatccg cttgagcaaa gccctagtat atctatggaa        540
cctgttagta tcaatgaaac aggaagcgca tatacaacta cgaacacagc actaaacgat        600
attgacattc cattctccat caatgagttg aacgagctat acaaacaagt atcttcgcat        660
aactcacatt cacaataa                                                      678
```

```
<210> SEQ ID NO 4
<211> LENGTH: 225
<212> TYPE: PRT
<213> ORGANISM: Saccharomyces cerevisiae

<400> SEQUENCE: 4

Met Val Val Ile Asn Gly Val Lys Tyr Ala Cys Glu Thr Cys Ile Arg
1               5                   10                  15

Gly His Arg Ala Ala Gln Cys Thr His Thr Asp Gly Pro Leu Gln Met
            20                  25                  30

Ile Arg Arg Lys Gly Arg Pro Ser Thr Thr Cys Gly His Cys Lys Glu
        35                  40                  45

Leu Arg Arg Thr Lys Asn Phe Asn Pro Ser Gly Gly Cys Met Cys Ala
    50                  55                  60

Ser Ala Arg Arg Pro Ala Val Gly Ser Glu Glu Asp Glu Thr Arg Cys
65                  70                  75                  80

Arg Cys Asp Glu Gly Glu Pro Cys Lys Cys His Thr Lys Arg Lys Ser
                85                  90                  95

Ser Arg Lys Ser Lys Gly Gly Ser Cys His Arg Arg Ala Asn Asp Glu
            100                 105                 110

Ala Ala His Val Asn Gly Leu Gly Ile Ala Asp Leu Asp Val Leu Leu
        115                 120                 125

Gly Leu Asn Gly Arg Ser Ser Asp Val Asp Met Thr Thr Thr Leu Pro
    130                 135                 140

Ser Leu Lys Pro Pro Leu Gln Asn Gly Glu Ile Lys Ala Asp Ser Ile
145                 150                 155                 160

Asp Asn Leu Asp Leu Ala Ser Leu Asp Pro Leu Glu Gln Ser Pro Ser
                165                 170                 175

Ile Ser Met Glu Pro Val Ser Ile Asn Glu Thr Gly Ser Ala Tyr Thr
            180                 185                 190

Thr Thr Asn Thr Ala Leu Asn Asp Ile Asp Ile Pro Phe Ser Ile Asn
        195                 200                 205

Glu Leu Asn Glu Leu Tyr Lys Gln Val Ser Ser His Asn Ser His Ser
    210                 215                 220

Gln
225

<210> SEQ ID NO 5
<211> LENGTH: 2085
<212> TYPE: DNA
<213> ORGANISM: Saccharomyces cerevisiae
```

<400> SEQUENCE: 5

```
atggtcttga taaatggcat aaagtatgcc tgtgagaggt gcataagagg ccatagagta      60
acaacatgca atcatacaga tcaaccgctt atgatgatca aacccaaagg tagaccttcc     120
actacatgcg actattgtaa acaacttcga aaaacaaga atgcaaatcc tgaaggtgtt      180
tgcacgtgtg gccggctaga agaaaaaaa ctggcacaga aagccaaaga agaagcaaga     240
gctaaagcca agaaaaaaca agaaaaacag tgtacctgcg ggactgatga ggtttgcaaa     300
tatcatgctc aaaagagaca tctaagaaag tccccttcaa gttctcaaaa gaaaggaaga     360
tccatttctc gttctcaacc aatgtttgaa agggtattgt cttctacttc acttgacagc     420
aatatgttat ccggccacgg agcactatca gatacctcta gcatactgac gagcacattt     480
ttagacagtg agccgggtgt tggtaaaatt tcaaaagatt accatcatgt cccttcattg     540
gcctccattt catccttaca atcctcgcaa tcgttagatc aaaatttcag tataccacaa     600
agcccgccgt tatcttcaat gtcatttaat tttctcacgg gaaatatcaa tgaaaccaac     660
caaaatcaca gtaatcatca gcattcaaaa tcaggcaata actggcaaga tagttcggta     720
agcttgccag cgaaagctga ttcacgtctt aacatgatgg ataaaaacaa ctctgtgggt     780
cttgacctat taggccattc aaaacgaata tcgccgatat caaactctcg tgtgggcgaa     840
gttagcgttc cgctagaaga atatattcct tctgacattg atggggttgg aagagttact     900
gataaaagct ctttggtcta cgattggcca tttgatgaaa gtattgagag aaatttcagt     960
acaaccgcaa ccgctgcaac tggtgaaagt aagttcgaca ttaacgacaa ctgtaataga    1020
attaatagca aaagttatag taagactaat agtatgaatg aaacggtat gaacaatagc     1080
aataataata atatcaacag taatggcaac gacaagaaca ataacaactc ttctagacaa    1140
gaacatcaag gaaatggact atttgacatg tttacagatt catcgtcgat ttcaacgctt    1200
tcccgtgcaa acttattatt gcaagaaaaa attggttcgc aagaaaactc tgtcaaacaa    1260
gaaaactatt cgaaaaatcc tcaacttcgt catcaattaa cttccagaag tagatcattt    1320
attcatcatc cggcaaacga gtatttgaag aatactttg gaaattcaca tagtaatgac    1380
atcggaaagg gagttgaagt gctatctttg acaccgagtt ttatggatat tcccgaaaaa    1440
gaaagagaaa cggaaagatc gccatcatcc aattacatta ctgacagacc tttcactcga    1500
aaacctagat cttctaacat tgacgtaaac cataggtatc cacctatggc accaacaacc    1560
gtagcgacat ctcccggtgc attgaacaat gccgtagcaa gcaatctcga cgatcaactg    1620
agtttaacat cactaaactc tcagccatca tcgatagcaa atatgatgat ggacccttca    1680
aacctagctg agcaaagttc tattcattca gttcctcagt caataaactc tccgagaatg    1740
cctaaaactg gaagtcgcca agacaagaac attcacacta gaaggaaga aagaaatccg    1800
ctaaataaca tacacgatct gtcacaattg gaaaatgtac cagacgagat gaaccaaatg    1860
ttctccccac cattaaaaag tatgaataga ccggatgcca taagggaaaa ttcatctagt    1920
agtaatttca taatccaagg aaatagcatg atctctacgc cttccggaag gaatgacctt    1980
ccagatacct ctccaatgag tagtattcaa acagcgtcac caccaagtca attactgacc    2040
gatcaaggat ttgcggattt ggataatttc atgtcttcgt tatga                   2085
```

<210> SEQ ID NO 6
<211> LENGTH: 694
<212> TYPE: PRT
<213> ORGANISM: Saccharomyces cerevisiae

<400> SEQUENCE: 6

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Ala Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Ile Pro Gln Ser Pro Pro Leu Ser Ser Met Ser
        195                 200                 205

Phe Asn Phe Leu Thr Gly Asn Ile Asn Glu Thr Asn Gln Asn His Ser
210                 215                 220

Asn His Gln His Ser Lys Ser Gly Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
370                 375                 380

Asn Gly Leu Phe Asp Met Phe Thr Asp Ser Ser Ile Ser Thr Leu
385                 390                 395                 400

Ser Arg Ala Asn Leu Leu Leu Gln Glu Lys Ile Gly Ser Gln Glu Asn
                405                 410                 415

```
Ser Val Lys Gln Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Asn Ile Asp Val Asn His Arg
            500                 505                 510

Tyr Pro Pro Met Ala Pro Thr Thr Val Ala Thr Ser Pro Gly Ala Leu
        515                 520                 525

Asn Asn Ala Val Ala Ser Asn Leu Asp Asp Gln Leu Ser Leu Thr Ser
    530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
        675                 680                 685

Asn Phe Met Ser Ser Leu
    690

<210> SEQ ID NO 7
<211> LENGTH: 357
<212> TYPE: DNA
<213> ORGANISM: Saccharomyces cerevisiae

<400> SEQUENCE: 7
atggctgaga acgtactct tatagctgtg atagctgacg aagatactac aactggttta    60
ttgttagccg ggattggaca atcactcct gaaacccaag aaaagaactt ttttgtttac   120
caagaaggta agactactaa ggaggaaatc actgacaagt taatcactt cactgaagag   180 agagacgata ttgccatcct tctaatcaac aacatatcg cggaaaacat aagagctaga   240
gtggactcct tcaccaatgc gttccctgct attttagaaa ttccatctaa agatcatccc   300
tacgaccctg aaaaggactc tgtattgaag agagtcagaa agttgttcgg tgagtaa     357

<210> SEQ ID NO 8
<211> LENGTH: 118
<212> TYPE: PRT
<213> ORGANISM: Saccharomyces cerevisiae
```

<400> SEQUENCE: 8

```
Met Ala Glu Lys Arg Thr Leu Ile Ala Val Ile Ala Asp Glu Asp Thr
1               5                   10                  15

Thr Thr Gly Leu Leu Leu Ala Gly Ile Gly Gln Ile Thr Pro Glu Thr
            20                  25                  30

Gln Glu Lys Asn Phe Phe Val Tyr Gln Glu Gly Lys Thr Thr Lys Glu
        35                  40                  45

Glu Ile Thr Asp Lys Phe Asn His Phe Thr Glu Arg Asp Asp Ile
    50                  55                  60

Ala Ile Leu Leu Ile Asn Gln His Ile Ala Glu Asn Ile Arg Ala Arg
65                  70                  75                  80

Val Asp Ser Phe Thr Asn Ala Phe Pro Ala Ile Leu Glu Ile Pro Ser
                85                  90                  95

Lys Asp His Pro Tyr Asp Pro Glu Lys Asp Ser Val Leu Lys Arg Val
            100                 105                 110

Arg Lys Leu Phe Gly Glu
        115
```

<210> SEQ ID NO 9
<211> LENGTH: 627
<212> TYPE: DNA
<213> ORGANISM: Saccharomyces cerevisiae

<400> SEQUENCE: 9

```
atgtcttcta gaaaaaaaaa tattttgaaa gtaatcatcc taggtgactc tggtgttggg      60
aagacctcct tgatgcaccg ttatgtcaat gataagtatt ctcaacagta taaagcaaca     120
attgggctg acttttttaac aaaagaggtg acagttgacg gtgataaagt tgccaccatg     180
caagtttggg atactgctgg acaggaacgt ttccaatcac tgggtgttgc tttctataga     240
ggtgcagatt gttgcgtttt ggtctacgat gtgaccaatg ccagttcctt tgagaatatt     300
aagtcttggc gagatgaatt tctagtgcat gcgaacgtaa actcaccaga aacatttcca     360
tttgttatac tgggaaataa aattgatgcc gaagaatcta aaaaaattgt atcagaaaag     420
tccgctcagg agcttgctaa atcattaggc gatattcctt tgttttaac aagtgccaaa     480
aacgctataa acgttgatac cgcatttgaa gaaattgcaa ggagtgcttt acaacagaat     540
caagctgata cagaagcctt tgaagatgac tataatgatg ccatcaatat tcgcctagat     600
ggagaaaata ttcttgtag ctgttga                                          627
```

<210> SEQ ID NO 10
<211> LENGTH: 208
<212> TYPE: PRT
<213> ORGANISM: Saccharomyces cerevisiae

<400> SEQUENCE: 10

```
Met Ser Ser Arg Lys Lys Asn Ile Leu Lys Val Ile Ile Leu Gly Asp
1               5                   10                  15

Ser Gly Val Gly Lys Thr Ser Leu Met His Arg Tyr Val Asn Asp Lys
            20                  25                  30

Tyr Ser Gln Gln Tyr Lys Ala Thr Ile Gly Ala Asp Phe Leu Thr Lys
        35                  40                  45

Glu Val Thr Val Asp Gly Asp Lys Val Ala Thr Met Gln Val Trp Asp
    50                  55                  60

Thr Ala Gly Gln Glu Arg Phe Gln Ser Leu Gly Val Ala Phe Tyr Arg
65                  70                  75                  80
```

-continued

```
Gly Ala Asp Cys Cys Val Leu Val Tyr Asp Val Thr Asn Ala Ser Ser
             85                  90                  95

Phe Glu Asn Ile Lys Ser Trp Arg Asp Glu Phe Leu Val His Ala Asn
            100                 105                 110

Val Asn Ser Pro Glu Thr Phe Pro Phe Val Ile Leu Gly Asn Lys Ile
            115                 120                 125

Asp Ala Glu Glu Ser Lys Lys Ile Val Ser Glu Lys Ser Ala Gln Glu
        130                 135                 140

Leu Ala Lys Ser Leu Gly Asp Ile Pro Leu Phe Leu Thr Ser Ala Lys
145                 150                 155                 160

Asn Ala Ile Asn Val Asp Thr Ala Phe Glu Glu Ile Ala Arg Ser Ala
                165                 170                 175

Leu Gln Gln Asn Gln Ala Asp Thr Glu Ala Phe Glu Asp Asp Tyr Asn
                180                 185                 190

Asp Ala Ile Asn Ile Arg Leu Asp Gly Glu Asn Asn Ser Cys Ser Cys
            195                 200                 205
```

CAUSATIVE GENES CONFERRING ACETIC ACID TOLERANCE IN YEAST

The present invention relates to genes conferring acetic acid tolerance in yeast. More specifically, the invention relates to the use of DOT5, preferably in combination with CUP2 and/or HAA1 to obtain acid tolerance in yeast. Even more preferably, the invention relates to specific alleles of said genes, and to yeast strains comprising said specific alleles.

Hydrolysates of lignocellulose are an interesting source for the production of bioethanol. However, one of the problems is the presence of toxic compounds such as acetic acid, furfural and lignin derivatives. Resistance against these inhibitors is essential for an efficient bioethanol production (Olsson and Hahn-Hägerdal, 1993). Especially acetic acid is known to have an inhibitory effect (Limtong et al., 2000). However, although overexpression of a single gene may improve acetic acid tolerance (Tanaka et al., 2012), it is important to understand the interplay of genes, proteins and other components that determine the physiological properties of a microorganism.

In the past, research focussed indeed primarily on the identification of single alleles or genetic loci that are involved in physiological traits (Glazier et al., 2002). However, in contrast to Mendelian traits (traits that are caused by one single locus), quantitative traits are caused by multiple genetic loci, which makes the unraveling of these complex traits rather difficult (Steinmetz et al., 2002). In addition, the genetic mapping of quantitative trait loci (QTL) is hampered by genetic heterogeneity, variable phenotypic contributions of each QTL, epistasis and gene-environment interactions (Flint and Mott, 2001). These limitations have facilitated the development of novel technologies to simultaneously identify genomic loci that are involved in complex traits. With these technologies, phenotypes like high-temperature tolerance, efficient sporulation and chemical resistance have been genetically unraveled (Steinmetz et al, 2002; Deutschbauer and Davies, 2005; Ehrenreich et al., 2010).

Recently, Swinnen et al. (2012) developed such a strategy, which was successfully employed to identify genetic determinants that are involved in high ethanol tolerance in the yeast *Saccharomyces cerevisiae*. In this strategy, called pooled-segregant whole-genome sequence analysis, it was demonstrated that QTLs underlying a complex trait can be mapped using small populations of segregants. However, the identification of causative mutations in these QTLs remains cumbersome since this method results in a relatively large size of the identified loci, which infers the analysis of a large number of genes. Reducing the size of QTLs can be achieved with inbreeding crosses, as was recently described by Parts et al (2011). However, the use of very large pools makes it an extensive procedure, especially since phenotyping industrially relevant traits often requires elaborate procedures, making the use of large numbers of segregants undesirable. Furthermore, although inbreeding crosses can be used to decrease the size QTLs, it remains unknown how it influences the mapping of minor loci.

In order to investigate the effect of inbreeding crosses on QTL mapping of industrially relevant strains, we have applied the pooled-segregant whole-genome sequencing analysis methodology on F1 and F7 segregants of a cross between a yeast strain that is superior for acetic acid tolerance and an industrial strain that is inferior for the same trait. Acetic acid tolerance is an industrially important characteristic as yeast fermentation is severely inhibited by this weak organic acid. As mentioned above, the presence of acetic acid in lignocellulosic hydrolysate strongly affects the fermentative capacity of yeast (Casey et al., 2010; Huang et al., 2011; Narendranath et al, 2001; Taherzadeh et al., 1997; Almeida et al., 2007). Especially the fermentation of pentose sugars suffers from the presence of acetic acid (Caseay et al., 2010; Bellissimi et al, 2009; Matsushika and Sawayama, 2012), emphasizing the importance of high acetic acid tolerance to enable efficient conversion of all sugars in lignocellulosic hydrolysate into ethanol. However, multiple attempts to rationally engineer increased acetic acid tolerance in yeast were met with limited success as a high number of genes is involved in the response to acetic acid stress (Abott et al., 2007; Mira et al., 2010 a & b; Li and Yuan, 2010, Hasunuma et al., 2011; Zhang et al., 2011). Random approaches such as evolutionary engineering has rendered improved strains in terms of acetic acid tolerance (Koppram et al., 2012; Wright et al., 2011), but this method leads to overselection of a single trait and to possible loss of other important properties.

We found for the first time that increased recombination frequency indeed results in the expected smaller loci, but also in unexpected appearance and disappearance of QTLs, compared to QTL mapping without inbreeding crosses. Furthermore, combining individual whole-genome sequencing data of acetic acid tolerant segregants with bioinformatics analysis enabled QTL mapping to single gene level. Surprisingly, DOT5 plays an important role in acetic acid tolerance, preferably in combination with CUP2 and HAA1. Even more surprisingly, we were able to identify superior alleles of these genes, which confer an even higher acetic acid tolerance to the yeast.

A first aspect of the invention is the use of DOT5 to obtain acetic acid tolerance in yeast in yeast. Preferably, said use is the overexpression of the gene, and/or the use of a specific allele. Most preferably, said use is the use of a specific DOT5 allele. Preferably said specific DOT5 allele is encoding SEQ ID No. 2

Preferably, the use of DOT5 according to the invention is combined with the use of CUP2 and/or HAA1 and/or VMA7. Preferably, said use is the overexpression of the genes, and/or the use of specific alleles. Even more preferably, said CUP2 allele encodes SEQ ID No.4, said HAA1 allele encodes SEQ ID No.6 and said VMA7 allele encodes SEQ ID No. 8. Preferably, said yeast is a xylose fermenting yeast. A xylose fermenting yeast, as used here, can be a yeast that is naturally producing ethanol on the base of xylose, or it can be a yeast that is mutated and/or genetically engineered to ferment xylose and to produce ethanol on the base of xylose. Even more preferably, said yeast is selected from the group consisting of *Saccharomyces* sp., *Pichia* sp., *Candida* sp., *Pachysolen* sp. and *Spathaspora* sp. Most preferably, said yeast is a *Saccharomyces* sp. preferably a *Saccharomyces cerevisiae*.

Another aspect of the invention is the use of a HAA1 allele encoding SEQ ID No. 6 for obtaining acetic acid tolerance in yeast. Preferably, said HAA1 allele comprises SEQ ID No. 5 as coding region. Preferably, said yeast is a xylose fermenting yeast. A xylose fermenting yeast, as used here, can be a yeast that is naturally producing ethanol on the base of xylose, or it can be a yeast that is mutated and/or genetically engineered to ferment xylose and to produce ethanol on the base of xylose. Even more preferably, said yeast is selected from the group consisting of *Saccharomyces* sp., *Pichia* sp., *Candida* sp., *Pachysolen* sp. and *Spathaspora* sp. Most preferably, said yeast is a *Saccharomyces* sp. preferably a *Saccharomyces cerevisiae*.

Another aspect of the invention is a yeast strain comprising SEQ ID No.1 in combination with SEQ ID No.3 and/or SEQ ID No.5 and/or SEQ ID No. 7. Preferably, said yeast is a xylose fermenting yeast. Even more preferably, said yeast is selected from the group consisting of *Saccharomyces* sp., *Pichia* sp., *Candida* sp., *Pachysolen* sp. and *Spathaspora* sp. Most preferably, said yeast is a *Saccharomyces* sp. preferably a *Saccharomyces cerevisiae*.

EXAMPLES

Figure 1:
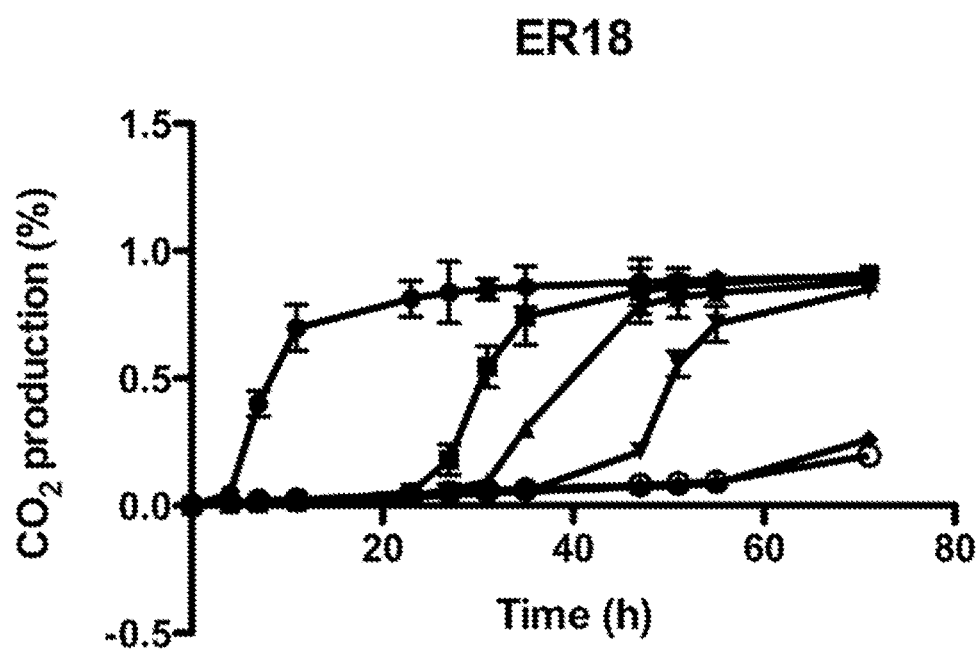
FIG. 1. Fermentation profiles of the acetic acid susceptible segregant Ethanol Red 18 (A) and the acetic acid tolerant segregant 16D (B). Strains were inoculated in YPD medium with 2% glucose at pH 4 and various concentrations of acetic acid; 0% (closed circle), 0.4% (closed square), 0.5% (closed upward triangle), 0.6% (closed downward triangle), 0.7% (closed diamond), 0.8% (open circle), 0.9% open square), 1.0% (open triangle). Data points are the average of duplicate measurements, error bars represent the maximum deviation of the average.
Figure 1:
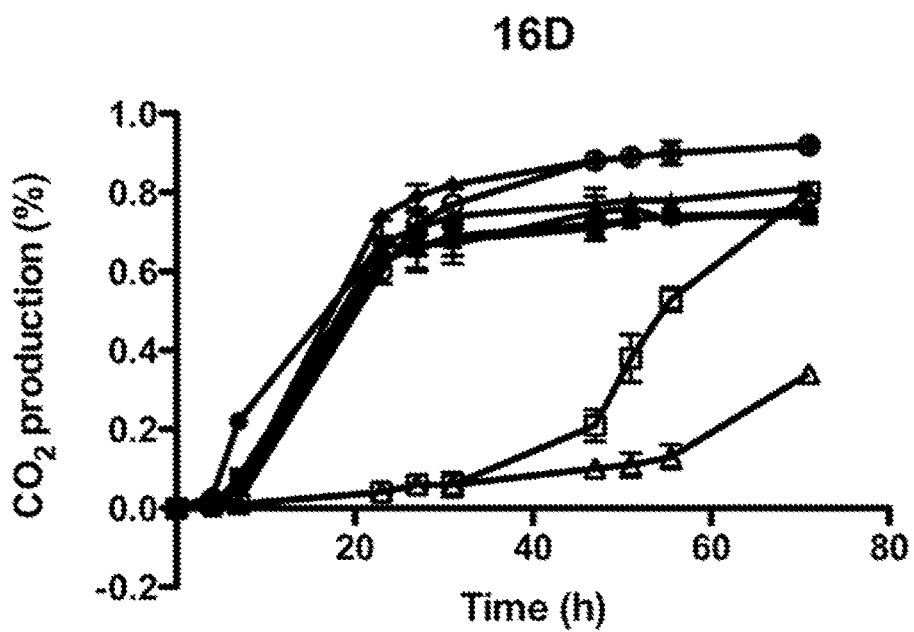

Material & Methods to the Examples
Strains and Growth Conditions
Strains and plasmids used in this study are shown in Table 1.

TABLE 1

| Strain | Description | Source |
| --- | --- | --- |
| Ethanol Red | Diploid strain used for industrial ethanol production, low acetic acid tolerance | Fermentis |
| JT22689 | Diploid strain isolated from fermenting must, high acetic acid tolerance | PYCC—Portuguese Yeast Culture Collection |
| ER18 | Haploid segregant from Ethanol Red with similar acetic acid tolerance, matα | This study |
| 16D | Haploid segregant from JT22689 with similar acetic acid tolerance, matα | This study |
| ER18 × 16D | Hybrid diploid strain obtained by crossing ER18 and 16D | This study |
| ER18 × 16D haa1Δ | Hybrid diploid strain; ER18 crossed with 16D haa1Δ | This study |
| ER18 haa1Δ × 16D | Hybrid diploid strain; ER18 haa1Δ crossed with 16D | This study |
| ER18 × 16D dot5Δ | Hybrid diploid strain; ER18 crossed with 16D dot5Δ | This study |
| ER18 dot5Δ × 16D | Hybrid diploid strain; ER18 dot5Δ crossed with 16D | This study |
| ER18 × 16D cup2Δ | Hybrid diploid strain; ER18 crossed with 16D cup2Δ | This study |
| ER18 cup2Δ × 16D | Hybrid diploid strain; ER18 cup2Δ crossed with 16D | This study |
| ER18 × 16D vma7Δ | Hybrid diploid strain; ER18 crossed with 16D vma7Δ | This study |
| ER18 vma7Δ × 16D | Hybrid diploid strain; ER18 vma7Δ crossed with 16D | This study |
| ER18 × 16D ypt7Δ | Hybrid diploid strain; ER18 crossed with 16D ypt7Δ | This study |
| ER18 ypt7Δ × 16D | Hybrid diploid strain; ER18 ypt7Δ crossed with 16D | This study |
| ER18 × 16D glo1Δ | Hybrid diploid strain; ER18 crossed with 16D glo1Δ | This study |
| ER18 glo1Δ × 16D | Hybrid diploid strain; ER18 glo1Δ crossed with 16D | This study |
| ER18 × 16D pma1Δ | Hybrid diploid strain; ER18 crossed with 16D pma1Δ | This study |
| ER18 pma1Δ × 16D | Hybrid diploid strain; ER18 pma1Δ crossed with 16D | This study |
| ER18 × 16D rav1Δ | Hybrid diploid strain; ER18 crossed with 16D rav1Δ | This study |
| ER18 rav1Δ × 16D | Hybrid diploid strain; ER18 rav1Δ crossed with 16D | This study |
| ER18 × 16D vtc4Δ | Hybrid diploid strain; ER18 crossed with 16D vtc4Δ | This study |
| ER18 vtc4Δ × 16D | Hybrid diploid strain; ER18 vtc4Δ crossed with 16D | This study |
| ER18 × 16D tos3Δ | Hybrid diploid strain; ER18 crossed with 16D tos3Δ | This study |
| ER18 tos3Δ × 16D | Hybrid diploid strain; ER18 tos3Δ crossed with 16D | This study |
| ER18_haa1(16D) | Strain ER18 in which HAA1 was replaced by superior allele from 16D | This study |
| ER18 ypt7Δ_haa1(16D) | ER18_haa1* carrying ypt7 deletion | This study |

Yeast cells were grown in a shaking incubator at 30° C. and 200 rpm in YPD medium containing 1% (w/v) yeast extract, 2% (w/v) Bacto peptone, and 2% (w/v) D-glucose.

Acetic acid medium was prepared by adding acetic acid to YPD medium, after which the pH was adjusted to 4.0 with HCl or KOH. Subsequently, the acetic acid medium was filtersterilized using a 0.2 μm filter. Antibiotics were added as required in the following final concentrations: geneticin, 400 μg/ml; nourseothricin, 150 μg/ml; chloramphenicol, 100 μg/ml. For solid medium, 1.5% Bacto agar was added to the YPD medium.

Fermentation experiments were performed in batch under near-anaerobic conditions in straight glass tubes containing 100 ml YPD medium and various concentrations of acetic acid. The culture was stirred continuously at 120 rpm using magnetic stirrers. Fermentations were inoculated with 5 ml of late-exponential phase yeast cells that were pre-cultured in YPD-medium (30° C., static incubation). The progress of the fermentation was monitored by measuring the decrease in weight of the fermentation tube+yeast cell culture. During fermentation, glucose present in the YPD medium is fermented, producing $CO_2$ that is emitted from the fermentation tubes. The emission of $CO_2$ is reflected by the loss in weight of the fermentation tube.

General Molecular Biology Techniques

Genomic DNA was extracted with PCI [phenol-chloroform-isoamyl-alcohol (25:24:1)] as described by Hoffman and Winston (1987). PCR reactions were performed with ExTaq (TAKARA) for diagnostic purposes or Phusion® High-Fidelity DNA polymerase (New England Biolabs) for sequencing purposes, both according to manufacturer's protocols. Yeast was transformed using the LiAc/PEG method described by Gietz et al 27. Gene deletions were made using a PCR-based strategy 28-29. After transformation, gene deletions were verified with PCR.

DNA Isolation for Whole-Genome Sequencing Analysis

The two parent strains ER18 and 16D and all segregants displaying high acetic acid tolerance were individually grown to stationary phase in 50 ml YPD-medium. Segregants were pooled, based on OD600, such that the number of cells from every segregant in the pool was equal. The genomic DNA was extracted according to Johnston30. At least 3 μg of genomic DNA was provided to the Beijing Genomics Institute (BGI) for sequencing analysis using the Illumina HiSeq2000 platform. Paired-end short reads of ~100 base pairs were generated for four samples (ER18, 16D, selected pool and unselected pool). The assembled sequences had an average coverage of 37X (ER18), 32X (16D) and 36X (selected and unselected pool). Mapping of the short read sequences, variant calling and QTL analysis were performed as described previously by Swinnen et al. 6 and by Hubmann et al. 7.

The SNP variant frequencies were calculated by dividing the number of the alternative variant by the total number of aligned reads. A very high or a very low frequency was indicative of a one-sided SNP segregation preferentially coming from one parent, indicating a genetic linkage to the trait of interest. Statistical confirmation of genetic linkage was obtained using EXPloRA (Duitama et al., in preparation) or by methods described earlier (Swinnen et al., 2012).

Scoring SNPs by Mismatch Mutation PCR

Individual SNPs were scored by PCR using forward and reverse primers that differ only at the 3' terminal nucleotide, based on the DNA sequence of ER18 or 16D. The optimal annealing temperature was determined by gradient PCR using DNA of ER18 and 16D. The optimal temperature is the annealing temperature at which only hybridization with primers containing an exact match was observed.

Mating, Sporulation, Tetrad Analysis

Mating, sporulation and tetrad analysis were performed by standard procedures 31. The mating type of the segregants was determined by diagnostic PCR for the MAT locus (Huxley et al., 1990).

Inbreeding Crosses

Inbreeding crosses were performed by random spore isolation, followed by mass mating. Random spore isolation was done by resuspending sporulating cells in 25 ml sterile MQ-water supplemented with 10 μg/ml zymolyase, 10 μl β-mercaptoethanol and glass beads. This cell suspension was incubated overnight in a shaking incubator (200 rpm). The cell suspension was subsequently vortexed for 5 minutes, followed by harvesting the spores with centrifugation (5 minutes, 3000 rpm, Beckman centrifuge). The spores were resuspended in 10 ml Nonidet P-40 (1.5% (v/v)) and put on ice for 15 minutes. After cooling, the suspension was sonicated four times (Amplitude=75%, cycle=1) for 30 seconds with two minute intervals. The suspension was washed three times with Nonidet P-40 and again sonicated four times. Spores were pelleted, resuspended in 300 μl MQ-water and plated in serial dilutions for single colonies. The remaining solution was plated on a single YPD-plate and incubated at 30° C. for two nights to allow mass mating of the isolated spores.

Confirming Involvement of Mutated Alleles in Superior Phenotype

Confirming the involvement of mutated alleles in the superior phenotype was done by reciprocal hemizygosity analysis (RHA) 6. For RHA, diploid strains were constructed by crossing ER18 and 16D wild type or derived deletion strains such that the hybrid diploid strain carried only one allele (either from ER18 or 16D) of the candidate gene. Subsequent fermentation experiments were performed with two individual isolates of the constructed diploids.

Example 1: Screening for Superior Acetic Acid Tolerance

Ethanol Red is a diploid yeast strain that is being used for bio-ethanol production at high temperatures, showing ethanol yields of up to 18%. However, the fermentation performance of this industrial yeast strain is severely affected by acetic acid, a weak organic acid present in high quantities in lignocellulosic hydrolysates. Haploid segregants were isolated from this yeast strain and scored on acetic acid tolerance by fermentation in YPD medium supplemented with various concentrations of acetic acid. It was observed that the maximum tolerance of Ethanol Red towards acetic acid was 0.6% (v/v) in YPD medium at a pH of 4.0. However, the lag phase was significantly prolonged by adding acetic acid to the growth medium, with a lag phase of approximately 30 hours at concentrations of 0.5% and 0.6% (FIG. 1). The haploid Ethanol Red segregant #18 (named ER18) showed similar tolerance to acetic acid and was therefore selected for further experiments.

In order to obtain a yeast strain with high acetic acid tolerance, the in-house yeast collection and the yeast collection from the Fungal Biodiversity Centre (CBS-KNAW, Utrecht, The Netherlands) were screened under acetic acid conditions. More than 1000 yeast strains were assessed, from which strain JT 22689 showed the best performance under fermentative conditions at high acetic acid concentrations, being able to ferment glucose in the presence of 0.9% acetic acid without a lag phase (not shown). Also from this strain a haploid segregant, named 16D, could be isolated that showed a similar phenotype in terms of acetic acid tolerance.

Example 2: QTL Mapping with Pooled F1 Segregants

Mapping the genetic determinants that are responsible for the high acetic acid tolerance of 16D was initiated by crossing the haploid segregants ER18 and 16D. The resulting hybrid strain was subsequently sporulated to obtain segregants that contain a mixture of the parental genomes. Obtained segregants were subsequently screened for high acetic acid tolerance, resulting in the identification of 27 (out of 288) segregants that were able to ferment glucose in the presence of 0.9% acetic acid, which is comparable with the tolerance observed for the superior parent strain. These 27 segregants were therefore selected for pooled-segregant whole-genome sequencing analysis. Genomic DNA isolated from the two parent strains, a pool of the 27 selected segregants and a control pool of 27 randomly selected segregants was sent for custom sequencing analysis using the Illumina HiSeq2000 technology (BGI, Hong Kong, China). The sequence reads from parent strains ER18 and 16D were aligned with the reference sequence from strain S288C. A total number of 23,150 SNPs between ER18 and 16D could be identified, which were subsequently filtered according to the method described by Duitama et al. (2012). The SNP variant frequencies were calculated by dividing the number of the alternative variant by the total number of aligned reads. The calculated variant frequencies were subsequently plotted against the respective chromosomal positions. The underlying structure in the SNP variant frequencies scatterplot of a given chromosome was identified by fitting smoothing splines in the generalized linear mixed model framework, as described by Claesen et al. (2013). Variant frequencies that significantly deviate from 50% (random segregation) are indicative of genetic linkage to the phenotype.

The results from the QTL mapping (depicted in FIG. 2) show two loci on the genome with a strong linkage to the superior segregant 16D: QTL1 on chromosome XIII and a second QTL on chromosome XVI. The statistical significance of QTL1 was confirmed using the Hidden Markov Model described previously, stretching from position 181019-294166. Both QTLs were further investigated by scoring selected SNPs in the 27 individual segregants in order to precisely determine the SNP variant frequencies and the statistical significance of the genetic linkage. Using a binomial test previously described (Swinnen et al., 2012; Claessen et al., 2013), both loci were found to be statistically significant. Furthermore, the size of both QTLs could be decreased to regions stretching from roughly 224000-277000 for QTL1 on chromosome XIII, and 568000-615000 for QTL2 on chromosome XVI.

Figure 3:
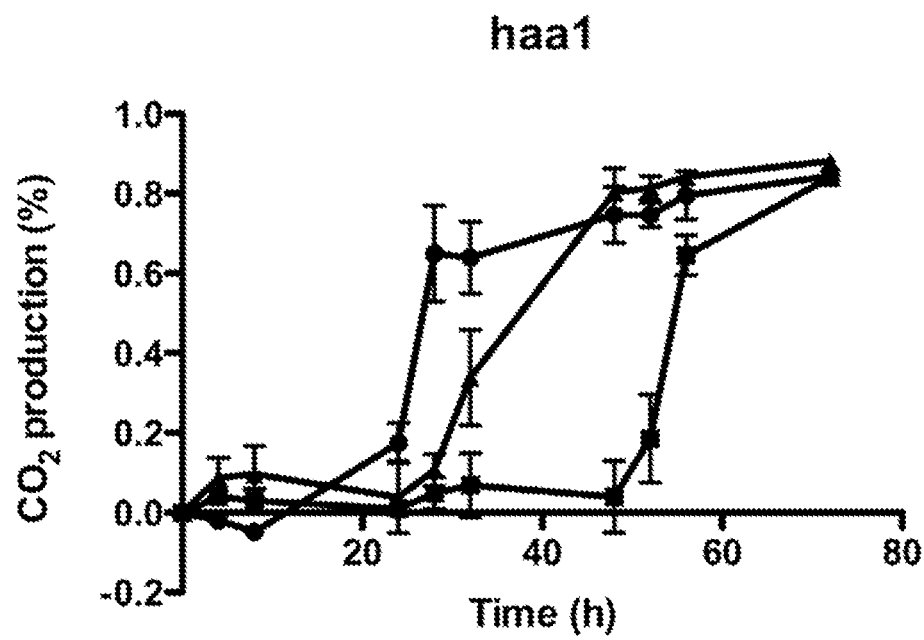
FIG. 3. Fermentation profiles of the reciprocal hemizygosity analysis on HAA1. Fermentations were performed in YPD medium supplemented with 0.7% acetic acid at pH 4.0. Three diploid hybrid strains were tested and compared: ER18Δhaa1×16D (circle); ER18×16DΔhaa1 (square); ER18×16D (triangle). Data points are the average of duplicate measurements. Error bars represent the maximum deviation of the average.

Example 3: Identification of Causative Genes by Reciprocal Hemizygosity Analysis in F1 QTLs For further analysis of the two identified QTLs, genes located within the linked regions were crosschecked with the *Saccharomyces* Genome Database. In QTL1, none of the genes were previously shown to play an important role in acetic acid tolerance. However, in QTL2, the gene HAA1 was located, a transcriptional activator known to be involved in adaptation to weak acid stress (Mira et al., 2010b; Fernandez et al., 2005). This gene was therefore further tested using the reciprocal hemizygosity analysis (RHA) method (Steinmetz et al., 2002). We constructed hemizygous diploid ER18/16D hybrid strains which contained a single copy of the superior or the inferior allele of HAA1, while the other copy of the gene was deleted. When these RHA strains were tested in fermentations with acetic acid, a clear difference was observed between the reciprocal strains. The HAA1 allele from the superior parent strain 16D sustained a much faster fermentation rate than the allele from the inferior parent strain ER18 (FIG. 3). In addition, a strain was constructed by replacing the whole HAA1 allele (promoter+ORF+terminator) from ER18 with the allele from 16D. Fermentations performed with this strain in the presence of several concentrations of acetic acid showed that the acetic acid tolerance was improved (results not shown). These results identify HAA1 as a causative allele in QTL2.

Example 4: QTL Mapping with Pooled F7 Segregants

It was observed that the two QTLs identified with the F1 pool were relatively large in size. Therefore, we attempted to narrow the QTLs by inbreeding F1 segregants obtained after sporulating the ER18/16D hybrid strain. Sporulating cells were harvested and haploid segregants were isolated using the random spore analysis method, after which the segregants were subjected to mass mating. A random amount of hybrid cells were subsequently sporulated again and the segregants isolated. This cycle of sporulation, isolating haploid segregants and mass mating was repeated six times, eventually resulting in the isolation of seventh generation (F7) segregants. These F7 segregants were screened for high acetic acid tolerance under the same conditions used for screening the F1 segregants. Out of 768 segregants assessed, 66 segregants showed good fermentation in the presence of 0.9% acetic acid. However, for statistical reasons, it was decided to construct a pool of similar size as the F1 pool to perform the pooled-segregant whole-genome sequencing analysis.

Figure 2:
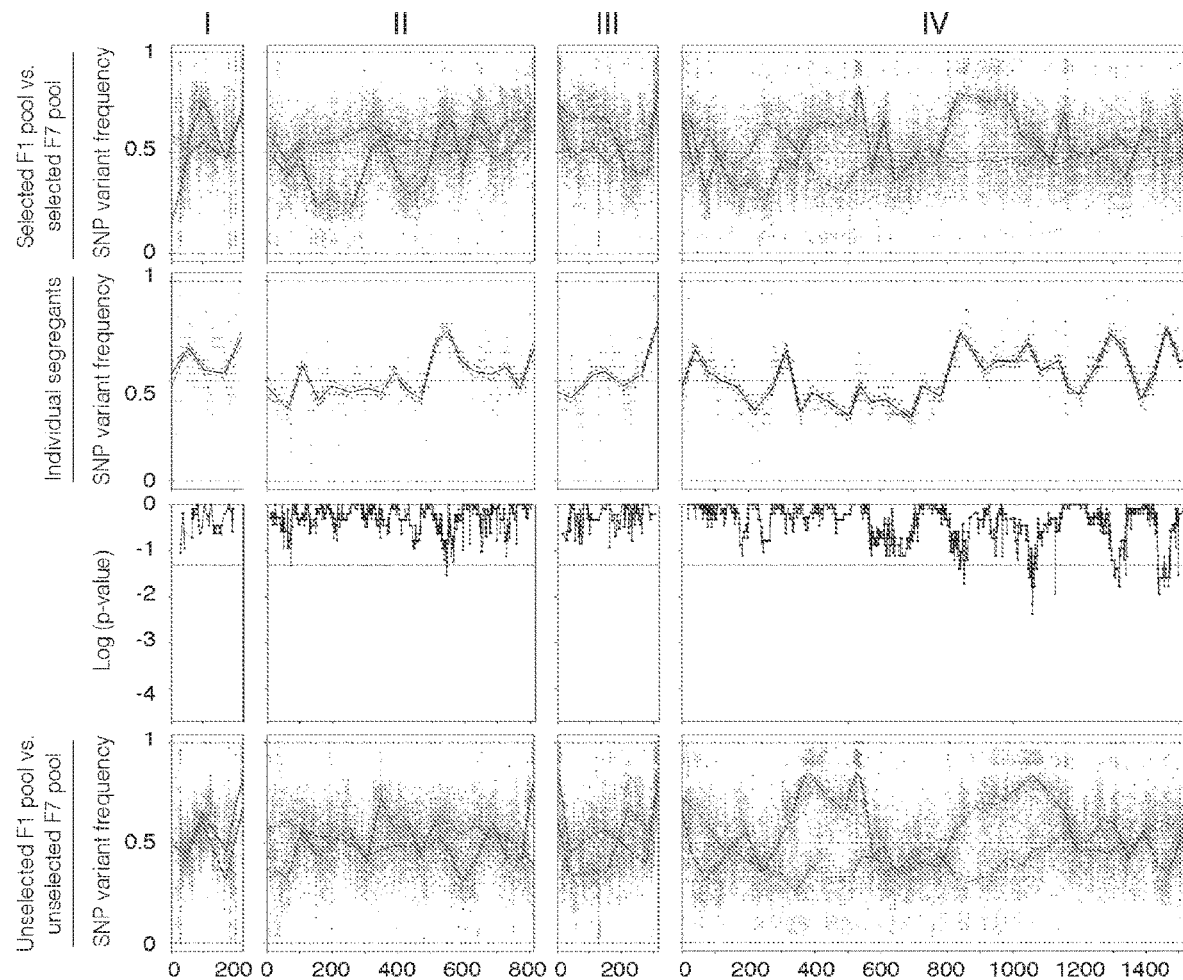
FIG. 2. QTL mapping of high acetic acid tolerance of pooled F1 segregants (green), pooled F7 segregants (red) and individual F7 segregants (black). Pooled F1 and pooled F7 segregants (27 segregants for both pools) were subjected to sequencing analysis utilizing the Illumina platform at BGI. Individual F7 segregants were sequenced with the Illumina platform at EMBL. Unselected pools consisting of 27 randomly selected segregants were also sequenced to eliminate linkage to inadvertently selected traits (BGI). P-values calculated using the individual sequencing data F7 segregants were plotted against the respective chromosomal position. $P<0.05$ was considered statistically significant.
Figure 2:
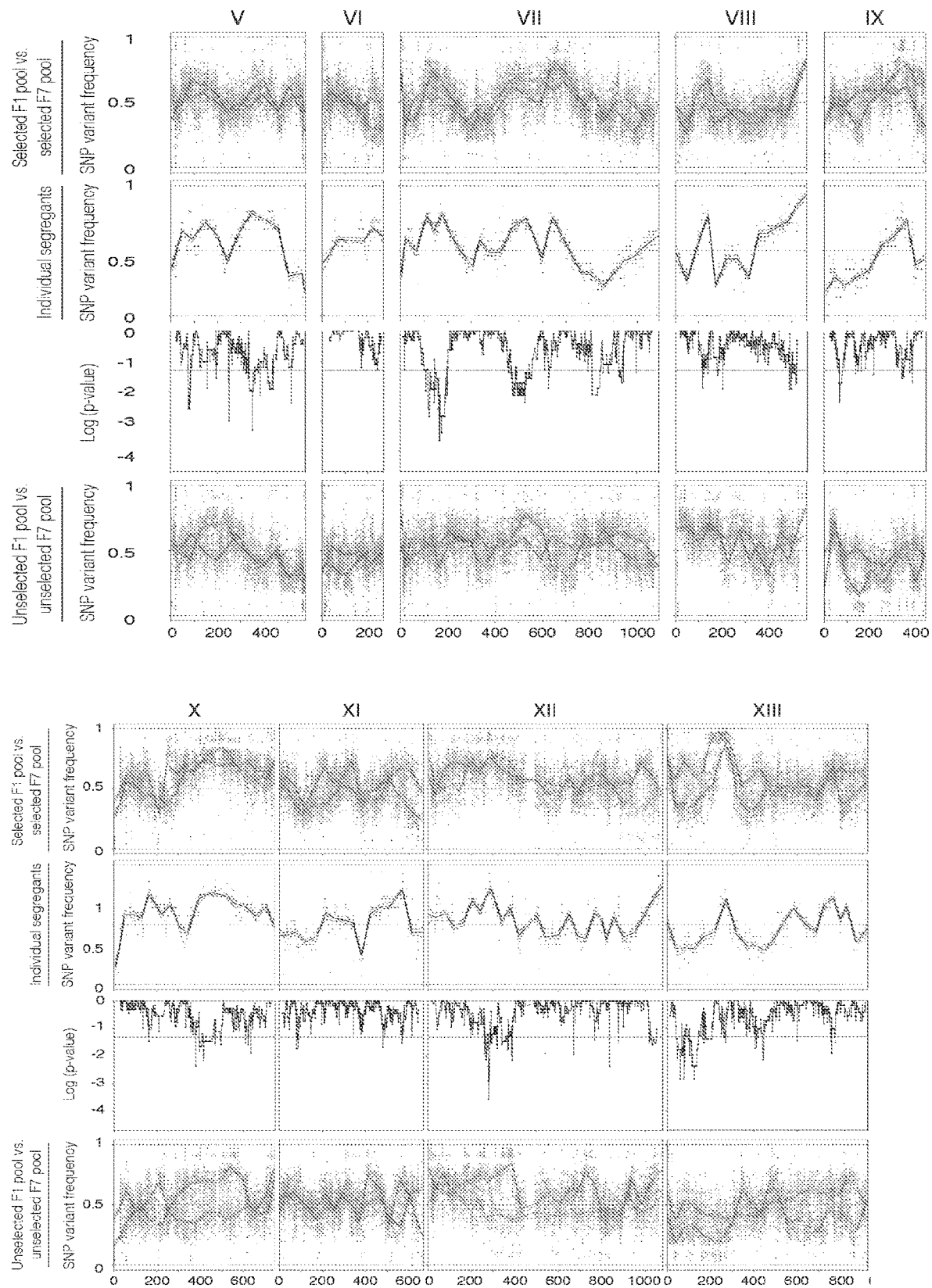
Figure 2:
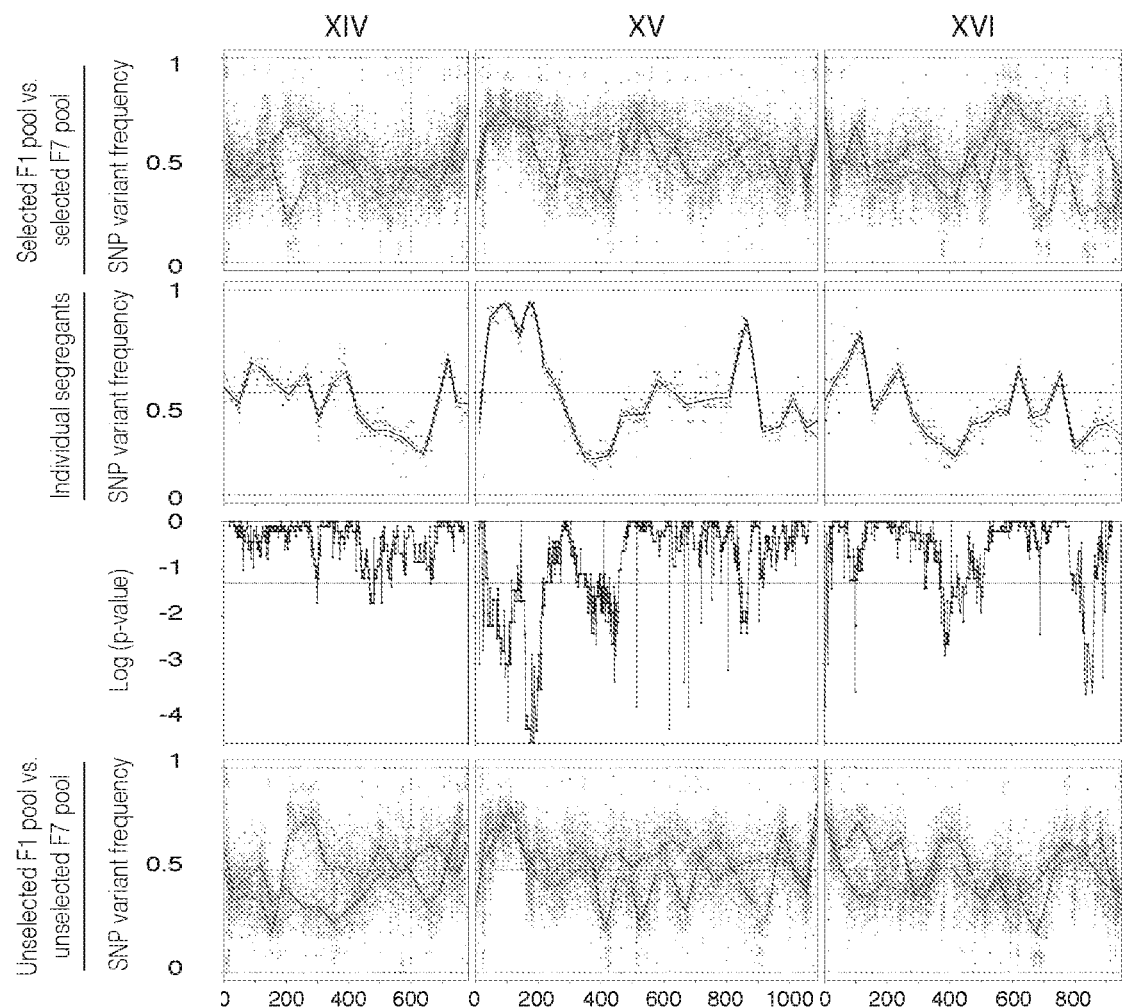

After analyzing and mapping the sequencing data, the data was compared with the mapping results obtained with the pool of F1 segregants (FIG. 2). As expected, the size of QTLs can be narrowed by increasing the recombination frequency through inbreeding crosses. The size of QTL1 on chromosome XIII obtained with F7 segregants was approximately 30 kb (position 247466-277019), which is 83 kb smaller than QTL1 obtained with F1 segregants. Moreover, the number of genes in the top of the locus significantly decreased compared to the F1 pool.

Surprisingly, increasing the recombination frequency also resulted in a number of unexpected outcomes. The second QTL identified with F1 segregants (chr. XVI) was no longer linked to the superior phenotype, as indicated by the decreased SNP variant frequencies calculated for this genomic region (FIG. 2). This indicates that the F7 segregants do not longer rely on the superior HAA1 gene from 16D to acquire higher acetic acid tolerance levels. It could therefore be expected that other alleles from 16D are causative for the superior phenotype. This notion was strengthened by the appearance of new peaks in the genetic mapping. Three new putative QTLs were identified, located on chromosome VII (QTL3), chromosome IX (QTL4) and chromosome X (QTL5).

Example 5: QTL Mapping with Individually Sequenced F7 Segregants

In an attempt to further enhance the resolution of QTL mapping, we sequenced the 27 segregants from the F7 pool individually. Genomic DNA samples were sent to the Genomic Core Facility of EMBL (Heidelberg, Germany) and the sequencing data was treated with the previously used scripts that were modified for this purpose (Duitama et al, unpublished). The main advantage of this approach is that the whole genome sequences of the 27 segregants can be compared with each other and that SNP variant frequencies can be calculated using the whole-genome sequences of the individual segregants, instead of calculating the frequencies from sequencing reads. Furthermore, by aligning the 27 whole-genome sequences we could score all SNPs in all single segregants compared to the inferior parent ER18 and calculate the statistical significance of every single SNP, using the binomial test described previously (Swinnen et al., 2012 Claessen et al., 2013).

FIG. 2 shows that the same QTLs could be identified using sequencing data from either the pooled segregants or the individual sequences, indicating that sequencing individual segregants yields comparable genetic maps with sequencing pooled segregants. However, additional information could be gained from the calculated p-values. SNPs are considered statistically significant if the p-value is lower than 0.05, and by combining the genetic mapping with the calculated p-values, a number of regions could be pinpointed that might contain the causative genes for acetic acid tolerance. Using this approach, we were able to find five regions on the genome that were statistically linked: QTL1 on chromosome XIII (position 261255-271498), QTL3 on chromosome VII (position 471171-554980), QTL4 on chromosome IX (position 335344-340345) and QTL5 on chromosome X (position 394527-451436). In addition, a new QTL could be identified on chromosome VII, stretching from position 107986-195096, making a total of 6 QTLs that contain potential superior alleles for acetic acid tolerance.

Example 6: Identification of Causative Genes by RHA in F7 QTLs

Figure 4:
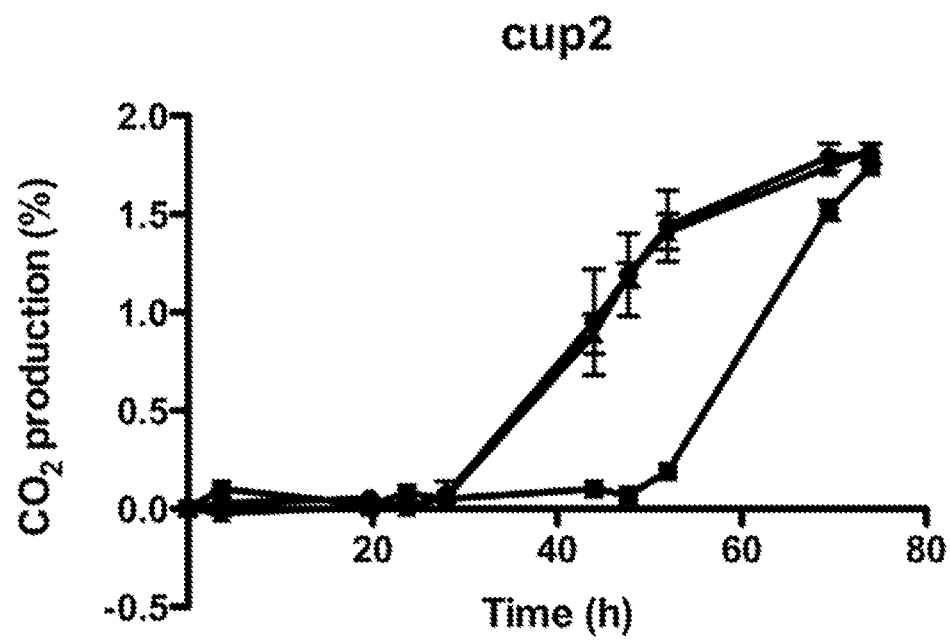
FIG. 4. Fermentation profiles of the reciprocal hemizygosity analysis on CUP2 (A), DOT5 (B) and VMA7 (C). Fermentations were performed in YPD medium supplemented with 0.7% acetic acid at pH 4.0. Three diploid hybrid strains were tested and compared: ER18Δ×16D (circle); ER18×16DΔ (square); ER18×16D (triangle). Data points are the average of duplicate measurements. Error bars represent the maximum deviation of the average.
Figure 4B:
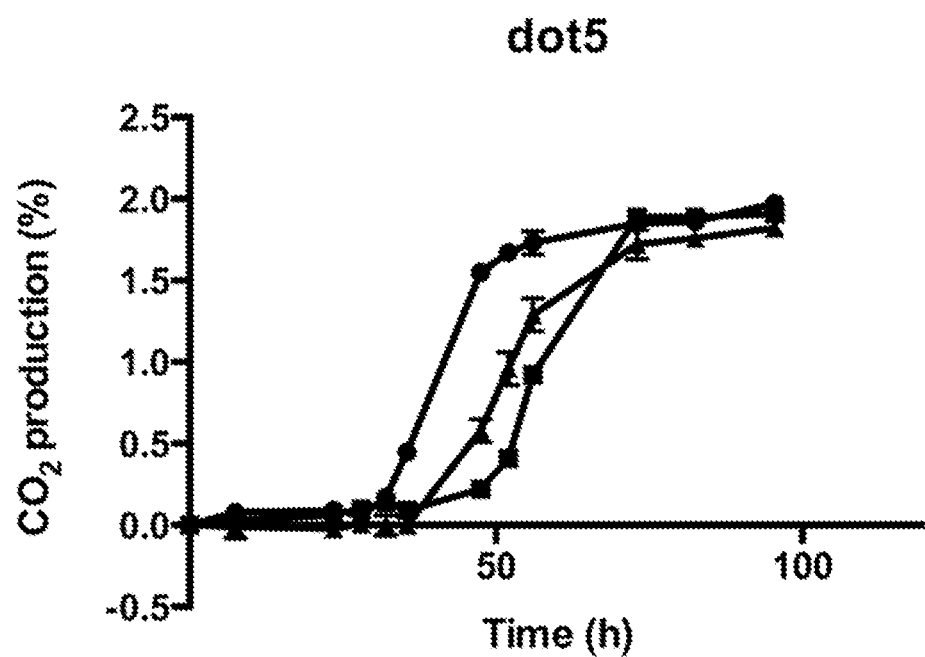
Figure 4C:
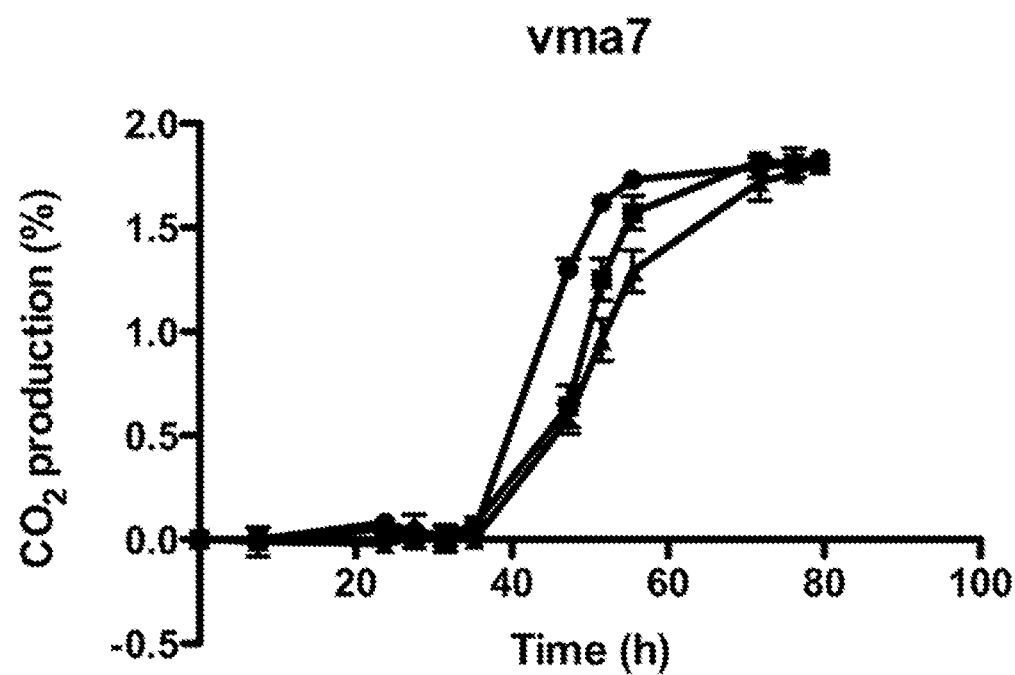

The identification of the causative genes located in the QTLs found with F7 segregants was performed similarly to the approach described for the F1 segregants. A number of candidate genes were selected based on their statistical linkage to the phenotype predicted by the p-values and their previously predicted role in acetic acid tolerance. The selected candidate genes were: PMA1 and VMA7 (QTL3), DOT5 (QTL4), RAV1 and VTC4 (QTL5), TOS3 and CUP2 (QTL6). These genes were subsequently tested by the reciprocal hemizygosity analysis method. After constructing the necessary strains, fermentation experiments were performed to assess the effect of the candidate genes on high acetic acid tolerance. The results of these fermentations, shown in FIG. 4, indicated that VMA7, DOT5 and CUP2 play an important role in the high acetic acid tolerance of segregant 16D. Furthermore, these results indicate that the combination of mapping SNPs and calculating the statistical significance of every SNP, using the whole-genome sequences of the individual segregants, strongly improves the resolution of QTL mapping.

Example 7: Natural Occurrence of Mutations in the Causative Genes

The sequences of the identified causative genes were compared with 28 strains from which the whole-genome sequences have been published. Only mutations between strain ER18 and strain 16D were considered; additional mutations between the strains examined were left out of the comparison. The results, summarized in Table 2, show that most mutations are not uncommon to the other yeast strains. Within the open reading frame of VMA7, no differences could be found between the sequences of ER18 and 16D. Therefore, the promoter sequences of the gene were investigated. Multiple mutations were identified, all of which could be found in the other strains examined.

The mutations identified in the ORFs of HAA1, DOT5 and CUP2 are commonly found the other strains. However, the mutation at position 574534 in HAA1 from 16D was not found in the other strains and may therefore be a novel and rather unique mutation.

Figure 5:
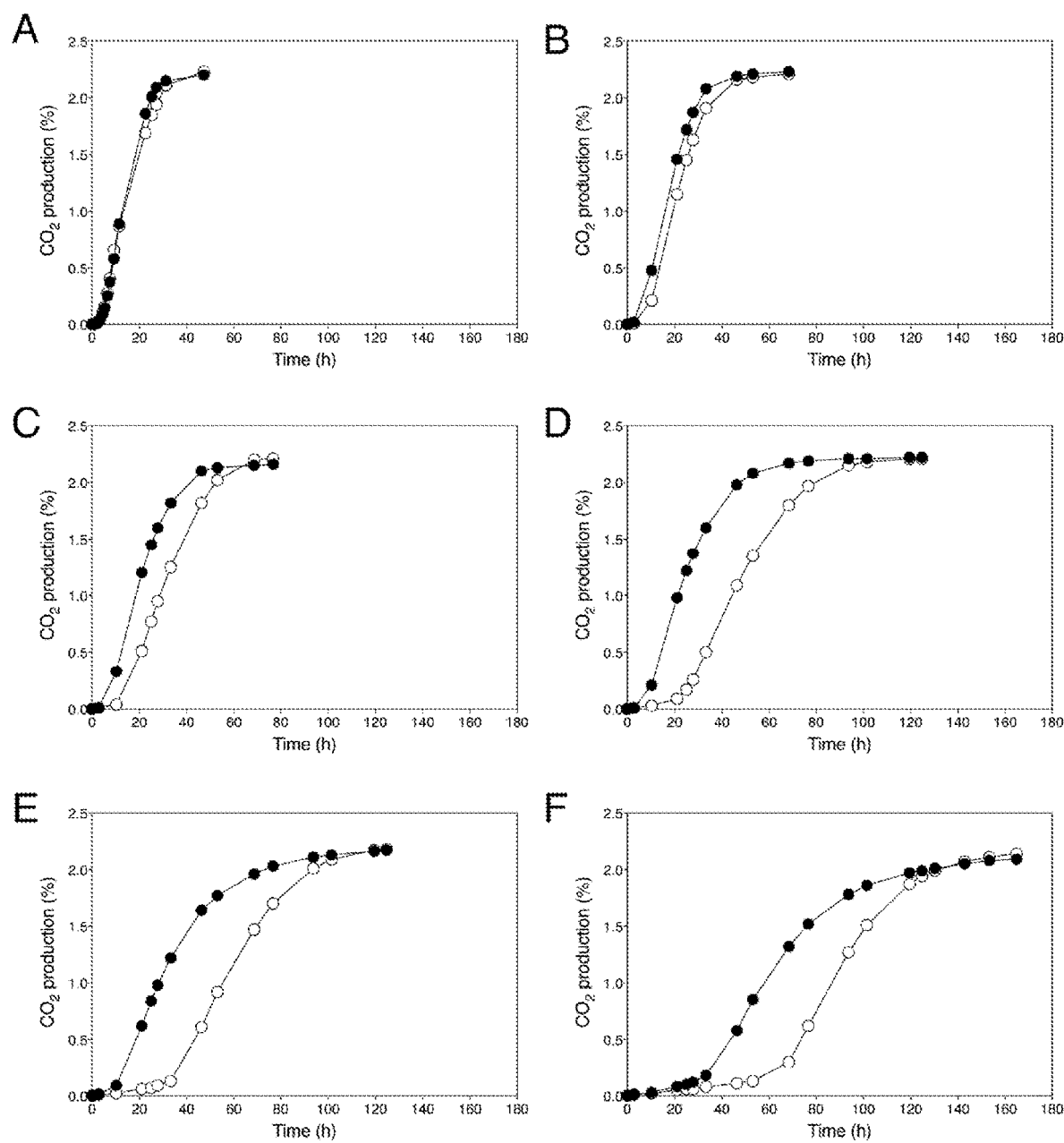
FIG. 5. Fermentation profiles of the diploid strains GSE16-T18 and GSE16-T18-HAA1* (carrying the unique HAA1 mutation of strain 16D in both HAA1 alleles). Fermentations were performed in YPD medium with 20% glucose and varying concentrations of acetic acid. Strains: GSE16-T18 (•) and GSE16-T18-HAA1* (○). (A) No acetic acid; (B) 1.0% acetic acid; (C) 1.2% acetic acid; (D) 1.4% acetic acid; (E) 1.6% acetic acid; (F) 2.0% acetic acid.

To confirm that this mutation is a causative allele in conferring high acetic acid tolerance, this point mutation was introduced into the two copies of the HAA1 allele of the industrial strain GSE16-T18 (which has the HAA1 allele of Ethanol Red). Fermentations were performed with YP+20% glucose in the presence of 1.0, 1.2, 1.4, 1.6 and 2.0% acetic acid at pH 5.2. In the absence of acetic acid there was no difference in the fermentation performance, while in the presence of whatever acetic acid concentration the performance of the GSE16-T18 HAA1* strain was consistently better than that of the GSE16-T18 strain. Especially the lag phase was strongly reduced by the HAA1* mutation, while the actual fermentation rate was not much affected. See FIG. 5.

Conclusions

Acetic acid is one of the major inhibitors in lignocellulose hydrolysates used for the production of second-generation bioethanol. Although several genes have been identified in laboratory yeast strains that are required for tolerance to acetic acid, the genetic basis of the high acetic acid tolerance naturally present in some Saccharomyces cerevisiae strains is unknown. Identification of its polygenic basis may allow improvement of the acetic acid tolerance of yeast strains used for second-generation bioethanol production by precise genome editing, minimizing the risk of negatively affecting other industrially-important properties of the yeast. Haploid segregants of a strain with unusually high acetic acid tolerance and a reference industrial strain were used as superior and inferior parent strain, respectively. After crossing of the parent strains, QTL mapping, using the SNP variant frequency determined by pooled-segregant whole-genome sequence analysis, revealed two major QTLs. All F1 segregants were then submitted to multiple rounds of random inbreeding and the superior F7 segregants were submitted to the same analysis, further refined by sequencing of individual segregants and bioinformatics analysis taking into account the relative acetic acid tolerance of the segregants. This resulted in disappearance in the QTL mapping with the F7 segregants of a major F1 QTL, in which we identified HAA1, a known regulator of high acetic acid tolerance, as a true causative allele. Novel genes determining high acetic acid tolerance, DOT5, CUP2, and a previously identified component, VMA7, were identified as causative alleles in the second major F1 QTL and in three newly appearing F7 QTLs, respectively. The superior HAA1 allele contained a single point mutation that was able by itself to improve acetic acid tolerance when inserted into an industrial yeast strain.

This work reveals the polygenic basis of high acetic acid tolerance in S. cerevisiae in unprecedented detail. It also shows for the first time that a single strain can harbour different sets of causative genes able to establish the same polygenic trait. The superior alleles identified can be used for improvement of acetic acid tolerance in industrial yeast strains.

TABLE 2

Occurrence of SNPs in the identified genes HAA1, VMA7, DOT5 and CUP2.

| | HAA1 ORF 573259 | ORF 573609 | ORF 573711 | ORF 574042 | ORF 574109 | ORF 574147 | ORF 574276 | ORF 574534 |
|---|---|---|---|---|---|---|---|---|
| ER18 | T | G | A | G | TC | T | C | G |
| 16D | C | A | G | A | AT | C | A | A |
| S288C | C | A | G | A | AT | C | A | G |
| AWRI1631 | C | A | G | A | AT | C | A | G |
| AWRI796 | C | A | G | A | AT | C | A | G |
| BY4741 | C | A | G | A | AT | C | A | G |
| BY4742 | C | A | G | A | AT | C | A | G |
| CBS7960 | C | A | G | A | AT | C | A | G |
| CEN.PK113 | C | A | G | A | AT | C | A | G |
| CLIB215 | C | A | G | A | AT | C | A | G |
| EC1118 | C | A | G | A | AT | C | A | G |
| EC9-8 | C | A | G | A | AT | C | A | G |
| FL100 | C | A | G | A | AT | C | A | G |
| FostersB | — | — | — | R | WY | Y | M | G |
| FostersO | — | — | — | A | TC | C | C | G |
| JAY291 | C | G | G | A | TC | C | A | G |
| Kyokai7 | T | G | A | G | TC | T | C | G |
| LalvinQA23 | — | — | — | — | WY | C | A | G |
| PW5 | C | G | A | A | TC | T | C | G |
| RM11-1a | C | A | G | A | AT | C | A | G |
| Sigma1278b | C | A | G | A | AT | C | A | G |
| T7 | T | G | A | G | TC | T | C | G |
| UC5 | C | G | A | G | TC | T | C | G |
| VL3 | — | A | G | A | AT | C | A | G |
| Vin13 | C | R | G | A | WY | C | A | G |
| W303 | C | A | G | A | AT | C | A | G |
| YJM269 | C | G | A | G | TC | T | C | G |
| YJM789 | C | G | A | G | TC | T | C | G |
| YPS163 | C | G | A | G | TC | T | — | G |
| ZTW1 | T | G | A | A | TC | T | C | G |

| | VMA7 Prom. 527390 | Prom. 527396 | Prom. 527439 | Prom. 527467 | Prom. 527618 | DOT5 ORF 334506 | ORF 335344 | CUP2 ORF 191489 | ORF 191625 |
|---|---|---|---|---|---|---|---|---|---|
| ER18 | G | C | G | T | G | G | C | G | T |
| 16D | T | T | C | A | A | A | T | A | C |
| S288C | T | T | C | A | A | A | C | A | C |
| AWRI1631 | T | T | C | A | A | A | T | A | C |

TABLE 2-continued

Occurrence of SNPs in the identified genes HAA1, VMA7, DOT5 and CUP2.

| Strain | | | | | | | | | |
|---|---|---|---|---|---|---|---|---|---|
| AWRI796 | T | T | C | A | A | A | C | A | C |
| BY4741 | T | T | C | A | A | A | C | A | C |
| BY4742 | T | T | C | A | A | A | T | A | C |
| CBS7960 | T | T | C | A | A | A | C | A | C |
| CEN.PK113 | T | T | C | A | A | A | T | A | C |
| CLIB215 | T | T | C | A | A | A | T | A | C |
| EC1118 | T | T | C | A | A | A | T | A | C |
| EC9-8 | T | T | C | A | A | A | C | A | C |
| FL100 | T | T | C | A | A | A | C | A | C |
| FostersB | T | T | C | A | A | A | – | R | C |
| FostersO | T | T | C | A | A | A | T | R | C |
| JAY291 | T | T | C | A | A | A | T | A | C |
| Kyokai7 | G | C | G | T | G | G | C | G | T |
| LalvinQA23 | C | T | T | A | A | A | – | A | C |
| PW5 | T | C | G | A | A | A | C | G | T |
| RM11-1a | T | T | C | A | A | A | T | A | C |
| Sigma1278b | T | T | C | A | A | G | C | A | C |
| T7 | T | C | G | A | A | A | C | G | T |
| UC5 | G | C | G | T | T | A | T | G | T |
| VL3 | T | T | C | A | G | G | C | A | C |
| Vin13 | T | T | C | A | A | A | T | A | C |
| W303 | T | T | C | A | A | A | T | A | C |
| YJM269 | G | C | G | A | A | A | C | G | T |
| YJM789 | T | T | C | A | A | A | C | A | C |
| YPS163 | T | C | G | A | T | A | T | G | T |
| ZTW1 | G | C | G | T | G | G | C | G | T |

The SNPs present in 16D compared to ER18 were checked in 28 strains of which the whole genome sequence has been published. SNPs present in the other strains compared to ER18, but not in 16D, are not presented.

Sequences
DOT5: SEQ ID No. 1/SEQ ID No. 2
CUP2: SEQ ID No. 3/SEQ ID No. 4
HAA1: SEQ ID No. 5/SEQ ID No. 6
VMA7: SEQ ID No. 7/SEQ ID No. 8
YPT7: SEQ ID No. 9/SEQ ID No. 10

REFERENCES

Abbott, D. A. et al. (2007). Generic and specific transcriptional responses to different weak organic acids in anaerobic chemostat cultures of Saccharomyces cerevisiae. Ferns Yeast Research 7, 819-833.

Almeida, J. R. M. et al. (2007). Increased tolerance and conversion of inhibitors in lignocellulosic hydrolysates by Saccharomyces cerevisiae. Journal og Chemical Technology and Biotechnology 82, 340-349.

Baudin, A., Ozier-Kalogeropoulos, O., Denouel, A., Lacroute, F. & Cullin, C. (1993). A simple and efficient method for direct gene deletion in Saccharomyces cerevisiae. Nucleic Acids Res 21, 3329-3330.

Bellissimi, E., van Dijken, J. P., Pronk, J. T. & van Maris, A. J. A. (2009). Effects of acetic acid on the kinetics of xylose fermentation by an engineered, xylose-isomerase-based Saccharomyces cerevisiae strain. Ferns Yeast Research 9, 358-364.

Casey, E., Sedlak, M., Ho, N. W. & Mosier, N. S. (2010). Effect of acetic acid and pH on the cofermentation of glucose and xylose to ethanol by a genetically engineered strain of Saccharomyces cerevisiae. Ferns Yeast Research 10, 385-393.

Claesen, J., Clement, L., Shkedy, Z., Foulquie-Moreno, M. R. & Burzykowski, T. (2013). Simultaneous mapping of multiple gene Loci with pooled segregants. PLoS One 8, e55133.

Deutschbauer, A. M. & Davis, R. W. (2005). Quantitative trait loci mapped to single-nucleotide resolution in yeast. Nat Genet 37, 1333-1340.

Duitama, J. et al. (2012). Fosmid-based whole genome haplotyping of a HapMap trio child: evaluation of Single Individual Haplotyping techniques. Nucleic Acids Res 40, 2041-53.

Ehrenreich, I. M. et al. (2010). Dissection of genetically complex traits with extremely large pools of yeast segregants. Nature 464, 1039-1042.

Fernandes, A. R., Mira, N. P., Vargas, R. C., Canelhas, I. & Sa-Correia, I. (2005). Saccharomyces cerevisiae adaptation to weak acids involves the transcription factor Haa1p and Haa1p-regulated genes. Biochem Biophys Res Commun 337, 95-103.

Flint, J. & Mott, R. (2001). Finding the molecular basis of quantitative traits: successes and pitfalls. Nat Rev Genet 2, 437-445.

Gietz, R. D., Schiestl, R. H., Willems, A. R. & Woods, R. A. (1995). Studies on the transformation of intact yeast cells by the LiAc/SS-DNA/PEG procedure. Yeast 11, 355-360.

Glazier, A. M., Nadeau, J. H. & Aitman, T. J. (2002). Finding genes that underlie complex traits. Science 298, 2345-2349.

Hasunuma, T. et al. (2011). Metabolic pathway engineering based on metabolomics confers acetic and formic acid tolerance to a recombinant xylose-fermenting strain of Saccharomyces cerevisiae. Microb Cell Fact 10, 2.

Hoffman, C. S. & Winston, F. (1987). A ten-minute DNA preparation from yeast efficiently releases autonomous plasmids for transformation of Escherichia coli. Gene 57, 267-272.

Huang, H. et al. (2011). Identification of crucial yeast inhibitors in bio-ethanol and improvement of fermentation at high pH and high total solids. Bioresour Technol 102, 7486-7493.

Hubmann, G. et al. (2013). Quantitative trait analysis of yeast biodiversity yields novel gene tools for metabolic engineering. Metab Eng 17, 68-81.

Huxley, C., Green, E. D. & Dunham, I. (1990). Rapid assessment of S. cerevisiae mating type by PCR. Trends Genet 6, 236.

Johnston, J. R. (1994). Molecular Genetics of Yeast: A Practical Approach, (Oxford University Press Inc., New York.

Koppram, R., Albers, E. & Olsson, L. (2012). Evolutionary engineering strategies to enhance tolerance of xylose utilizing recombinant yeast to inhibitors derived from spruce biomass. Biotechnol Biofuels 5, 32.

Li, B. Z. & Yuan, Y. J. (2010). Transcriptome shifts in response to furfural and acetic acid in Saccharomyces cerevisiae. Appl Microbiol Biotechnol 86, 1915-1924.

Lumtong, S., Sumpradit, T., Kitpreechavanich, V., Tuntirungkij, M., Seki, T. and Yoshida, T. (2000). Effect of Acetic acid on growth and ethanol fermentation of xylose fermenting yeasts and Saccharomyces cerevisiae. Kastaert J. (Nat. Sci) 34, 64-73.

Matsushika, A. & Sawayama, S. (2012). Characterization of a Recombinant Flocculent Saccharomyces cerevisiae Strain That Co-Ferments Glucose and Xylose: II. Influence of pH and Acetic Acid on Ethanol Production. Appl Biochem Biotechnol.

Mira, N. P., Palma, M., Guerreiro, J. F. & Sa-Correia, I. (2010a). Genome-wide identification of Saccharomyces cerevisiae genes required for tolerance to acetic acid. Microb Cell Fact 9, 79-91.

Mira, N. P., Becker, J. D. & Sa-Correia, I. (2010b). Genomic expression program involving the Haa1p-regulon in Saccharomyces cerevisiae response to acetic acid. OMICS 14, 587-601.

Narendranath, N. V., Thomas, K. C. & Ingledew, W. M. (2001). Effects of acetic acid and lactic acid on the growth of Saccharomyces cerevisiae in a minimal medium. J Ind Microbiol Biotechnol 26, 171-177.

Olsson, L. and Hahn-Hägerdal, B. (1993). Fermentative performance of bacteria and yeast in lignocellulose hydrolysates. Process Biochem. 28, 249-257.

Parts, L. et al. (2011). Revealing the genetic structure of a trait by sequencing a population under selection. Genome Res.

Sherman, F. & Hicks, J. (1991). Micromanipulation and dissection of asci. Methods Enzymol 194, 21-37.

Steinmetz, L. M. et al. (2002). Dissecting the architecture of a quantitative trait locus in yeast. Nature 416, 326-330.

Swinnen, S. et al. (2012). Identification of novel causative genes determining the complex trait of high ethanol tolerance in yeast using pooled-segregant whole-genome sequence analysis. Genome Res 22, 975-984.

Taherzadeh, M. J., Niklasson, C. & Lidén, G. (1997). Acetic acid—friend of foe in anaerobic batch conversion of glucose to ethanol by Saccharomyces cerevisiae. Chemical Engineering Science 52, 2653-2659.

Tanaka, K., Ishii, Y., Ogawa, J. And Shima, J. (2012). Enhancement of acetic acid tolerance in Saccharomyces cerevisiae by overexpression of the HAA1 gene, encoding a transcription factor. Appl. Environ. Microbiol. 78, 8161-8163.

Wach, A. (1996). PCR-synthesis of marker cassettes with long flanking homology regions for gene disruptions in S. cerevisiae. Yeast 12, 259-265.

Wright, J. et al. (2011). Batch and continuous culture-based selection strategies for acetic acid tolerance in xylose-fermenting Saccharomyces cerevisiae. Fems Yeast Research.

Zhang, J. G. et al. (2011). Improvement of acetic acid tolerance and fermentation performance of Saccharomyces cerevisiae by disruption of the FPS1 aquaglyceroporin gene. Biotechnol Lett 33, 277-284.

---

The invention claimed is:

1. A yeast strain comprising an overexpressed HAA1 allele encoding SEQ ID NO: 6.

2. A yeast strain according to claim 1, wherein the yeast strain further comprises a DOT5 allele encoding SEQ ID No. 2.

3. A yeast strain according to claim 1, wherein the yeast strain further comprises at least one of a CUP2 allele encoding SEQ ID No.4 and a VMA7 allele encoding SEQ ID No. 8.

4. A yeast strain according to claim 1, wherein the yeast strain is a *Saccharomyces* sp.

5. A yeast strain according to claim 4, wherein the *Saccharomyces* sp. is *Saccharomyces cerevisiae*.

6. A yeast strain according to claim 1, wherein the yeast strain is a xylose fermenting yeast strain.

7. A process for the production of ethanol comprising contacting a yeast strain according to claim 1 with xylose to produce ethanol.

* * * * *